United States Patent [19]

Ueno

[11] Patent Number: 5,071,838

[45] Date of Patent: Dec. 10, 1991

[54] TREATMENT OF SHOCK BY CYCLODEXTRINS AND THEIR DERIVATIVES

[75] Inventor: Ryuji Ueno, Hyogo, Japan

[73] Assignee: K. K. Ueno Seiyaku Oyo Kenkyujo, Osaka, Japan

[21] Appl. No.: 679,864

[22] Filed: Apr. 3, 1991

Related U.S. Application Data

[63] Continuation-in-part of Ser. No. 599,598, Oct. 18, 1990, abandoned.

[30] Foreign Application Priority Data

Oct. 18, 1989 [JP]  Japan ................................. 1-274425

[51] Int. Cl.$^5$ ............................................. A61K 31/70
[52] U.S. Cl. ..................................................... 514/23
[58] Field of Search ......................................... 514/23

[56] References Cited

U.S. PATENT DOCUMENTS 4,258,180  3/1981  Lewis et al. ....................... 536/112
4,877,778 10/1989  Carpenter et al. ................ 536/112

Primary Examiner—Stanley J. Friedman
Attorney, Agent, or Firm—Sughrue, Mion, Zinn, Macpeak & Seas

[57] ABSTRACT

A method for treatment of shock which comprises administering, to a subject in need of such treatment, a cyclodextrin or a derivative thereof in an amount effective in such treatment.

4 Claims, No Drawings

TREATMENT OF SHOCK BY CYCLODEXTRINS AND THEIR DERIVATIVES

This is a continuation-in-part of application No. 07/599,598 filed Oct. 18, 1990 now abandoned.

BACKGROUND OF THE INVENTION

1. Field of the Invention

The present invention relates to a method for treatment of shock which comprises administering a cyclodextrin or a derivative thereof to a subject.

Shock refers to a condition of acute circulatory failure and in other words a condition wherein cardiac function is seriously damaged by hemorrhage, bacterial toxin, pathological cardiac alternations, anaphylaxis etc. and cardiac output, which must be retained at a level essential for supporting normal function of organs, is reduced, thereby causing histonic circulatory failure and hence cellular metabolic disorder. Conventionally, shock symptoms have been treated by transfusion or administration of vasodilator etc., without satisfactory effect. Accordingly, there has been a continuous need of developing a medicament useful in treatment of shock.

As a result of extensive studies about the properties of cyclodextrin and their derivatives which have been used only as a complexing agent in the pharmaceutical field, the present inventor discovered that these compounds have beneficial action in prolonging the life of a patient who is in the condition of shock.

SUMMARY OF THE INVENTION

In a first aspect, the present invention provides a method for treatment of shock which comprises administering, to a subject in need of such treatment, a cyclodextrin or a derivative thereof (hereinafter, referred to as the compound used in the invention) in an amount effective in such treatment.

In a second aspect, the present invention provides a use of a cyclodextrin or a derivative thereof for the manufacture of a medicament for treatment of shock.

In a third aspect, the present invention provides a pharmaceutical composition for treatment of shock comprising a cyclodextrin or a derivative thereof in association with a pharmaceutically acceptable carrier, diluent or excipient.

DETAILED DESCRIPTION OF THE INVENTION

As used herein, the term "shock" refers to the condition as mentioned above and includes hypovolemic shock (traumatic shock) due to bleeding, thermal burn, dehydration etc., cardiogenic shock, endotoxic shock, and acute peripheral vasogenic shock, nerogeric shock, antigenic and drug induced shock due to hyperseneitivity and anaphylaxis, as well as a shock induced by hormonal insufficiency.

The term "treatment" includes prevention, cure and relief of disease and arrest or relief of development of disease.

The term "cyclodextrin" includes α-cyclodextrin, β-cyclodextrin and γ-cyclodextrin.

The term "derivatives" used in conjunction with the term cyclodextrin refers to compounds in which at least one atom selected from hydrogen, oxygen or carbon in the cyclodextrin molecule is replaced by an atom or a group of atoms ordinarily present as a substituent in this kind of organic compounds (saccharides). These derivatives include etherified cyclodextrins, branched cyclodextrins, acylated cyclodextrins and sulfur-containing cyclodextrins.

Said etherified cyclodextrins include (lower)-alkylcyclodextrins such as methylcyclodextrin, ethylcyclodextrin, propylcyclodextrin, dimathylcyclodextrin, trimethylcyclodextrin etc., (lower,alkenylcyclodextrins, hydroxy(lower)alkylcyclodextrins such as hydroxyethylcyclodextrin, hydroxyethylcyclodextrin etc., (lower)-alkoxy(lower)alkylcyclodextrins, aralkylcyclodextrins such as benzylcyclodextrin etc., halo(lower)alkylcyclodextrins such as chloroethylcyclodextrin etc., and cylodextrinepichlorohydrine copolymer and so on. These may be etherified cyclodextrins in which one, two or three hydroxy groups in any of the glucose units of the cyclodextrin molecule are converted into ether.

Said branched cyclodextrins include glucosylcyclodextrin, maltosylcyclodextrin etc.

Said acylated cyclodextrins include (lower)-alkanoylcyclodextrins such as formylcyclodextin, acetylcyclodextrin etc., aromatically or heterocyclically acylated cyclodextrins such as benzoylcyclodextrin, nicotinoylcyclodextrin etc.

Said sulfur-containing cyclodextrins include sulfonated cyclodextrins etc.

The derivatives of cyclodextrin include also derivatives in which two or more of derivatizations selected from etherification, branching, acylation and sulfuration are co-existing.

These derivatives are known or can be prepared by a method similar to that for the known derivatives.

The compounds used in the present invention may be used as a medicine for animals and human beings and usually applied systemically or locally by the method of oral administration, intravenous injection (including installation), subcutaneous injection, rectal administration and the like.

While the dosage of cyclodextrin or derivatives thereof will vary depending on age, weight, condition of particular subject, desired therapeutic effect etc., satisfactory effects will generally be obtained with the dosage of 1 μg/kg to 500 mg/kg, preferably 10 μg/kg to 50 mg/kg, administered once a day or 2 to 4 divided doses a day or as a sustained form. Administration may be effected by injection etc.

For administration, the compound used in the invention can be given in the form of conventional pharmaceutical preparation which contains said compound, as an active ingredient, in admixture with a pharmaceutically acceptable carrier such as organic or inorganic, solid or liquid excipients suitable for the desired mode of administration such as injection. Such preparation may be in a solid form such as solid from which a solution can be made up before use, etc. or in a liquid form such as solution, emulsion, suspension, etc. Said carrier includes starch, lactose, glucose, sucrose, dextrin cellulose, paraffin, aliphatic glyceride, water (distilled water, physiological saline, Ringer's solution etc.), alcohol, acacia etc. The above preparation may also contain auxiliary substance, stabilizer, emulsifier, dispersing agent, preservative, pH-adjuster, isotonic agent and other conventional additives added as necessary.

As solid composition of &his invention for oral administration, tablets, torches, luccals, capsule, pills, powders, granules and the like are included. The solid composition containing one or more active substances is mixed with at least an inactive diluent such as lactose, mannitol, glucose, hydroxypropyl cellulose, micro crystalline cellulose, starch, polyvinyl pyrolidone, magnesium aluminate metasilicate. The composition may contain additives other than the inactive diluent, such as lubricants e.g., magnesium stearate, a disintegrator e.g. cellulose calcium gluconates, stabilizers e.g. misoprotols or phospholipids. The stability may be often increased by forming lyposome with phospholipids. Tablets and pills may be coated with an enteric or gastrcenteric film such as white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed such as gelatin. Further, when rapid effect is required, it may be in the form of buccal, in which glycerol, lactose etc are used as a base.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents, suspending agents, sweeteners, flavors, perfumes and preservatives.

Another formulation according to the present invention is the rectal or vaginal suppository. This can be prepared by mixing at least one active compound according to the invention with a suppository base which may be softened at body temperature, optionally containing non-ion sufactant having appropriate softening temperature for improving absorption.

The present invention is illustrated in more detail by way of the following Examples and Test Examples.

EXAMPLE 1

| Dimethyl-α-cyclodextrin | 100 mg |
| Physiological saline q.s. to | 10 ml |

The above ingredients are brought into solution by conventional way to form an injectable solution.

EXAMPLE 2

| Dimethyl-α-cyclodextrin | 150 mg |
| Corn Starch | 45 mg |
| Lactose | 300 mg |
| Magnesium stearate | 5 mg |

The above ingredients are mixed, granulated, and pressed according to the conventional procedure to make tablets, which were then enterically coated.

EXAMPLE 3

| Hydroxypropyl-α-cyclodextrin | 200 mg |
| Physiological saline q.s. to | 10 ml. |

EXAMPLE 4

| Hydroxypropyl-α-cyclodextrin | 150 mg |
| Corn starch | 45 mg |
| Lactose | 300 mg |
| Magnesium stearate | 5 mg |

The above ingredients are mixed, granulated, and pressed according to conventional procedure to make tablets, which then enterically coated.

EXAMPLE 5

| Trimethyl-β-cyclodextrin | 200 mg |
| Lactose | 195 mg |
| Magnesium stearate | 5 mg |

The above ingredients are mixed according to the conventional procedure and filed in hard gelatin capsules.

EXAMPLE 6

| Hydroxypropyl-β-cyclodextrin | 300 mg |
| Physiological saline q.s. to | 10 ml. |

EXAMPLE 7

| β-cyclodextrin polymer | 300 mg |
| Physiological saline q.s. to | 10 ml. |

Test Example 1

Male Crj-Wister rats (weighing 230–240 g, 7 weeks old, 13–20 rats per groups) were used. Predetermined amounts of commercial dimethyl-=-cyclodextrin [a mixture mainly comprising hexakis(2,6-di-0-methyl)-α-cyclodextrin and pentakis(2,6-di-0-methyl)-mono(2,3,6-tri-O-methyl)-α-cyclodextrin; hereinafter referred to as DMCD]or pentakis[2,6-di-0-methyl)-mono(2,3,6-tri-0-methyl)-α-cyclodextrin (purified from commercial DMCD; hereinafter referred to as P-DMCD], dissolved in the Ringer solution (2 ml/kg) was intravenously administered. The control group received the same amount of Ringer solution.

After 5 minutes, lipopolyssacharide (15 mg/kg) was intravenously administered. After 24 hours, the rats were inspected for survival and rates were calculated. The results are shown in the following Table.

| | Survival rate | | | |
| | Commercial DMCD | | P-DMCD | |
| Dose (mg/kg) | Survival Animals/Total Animals | Survival Rate (%) | Survival Animals/Total Animals | Survival Rate (%) |
| 0 | 3/20 | 15 | — | — |
| 0.3 | 4/20 | 20 | 6/15 | 40 |
| 1 | 11/20 | 55 | 6/15 | 40 |
| 3 | 7/20 | 35 | 10/15 | 67 |
| 10 | 13/20 | 65 | 9/13 | 69 |
| 30 | 11/20 | 55 | — | — |

Test Example 2

The survival rate in the treatment with α-cyclodextrin (3 mg/kg) was determined as described in Test Example 1.

As a results, it was shown that the survival rate of α-cyclodextrin (3 mg/kg) group was 27% as compared with that of Ringer group which was 13%.

Test Example 3

Lipopolysaccharide (3.75 mg/kg) was intravenously administered to male Beagle dogs (weighing 7.5–9.5 kg) and, after 15 minutes, a solution of commercial DMCD (10 mg/kg) in the Ringer solution (0.5 ml/kg) was intravenously administered over five minutes in order to evaluate the activity of DMCD against endotoxin shock. The control groups (4 Beagle dogs per group) received the same amount of Ringer solution.

Two of four dogs of Ringer group died, while all four of the DMCD group survived.

Test Example 4

The survival rates in the treatment with dimethyl-$\beta$-cyclodextrin (10 mg/kg), hydroxypropyl-$\alpha$-cyclodextrin (1 mg/kg) and hydroxypropyl-$\beta$-cyclodextrin (10 mg/kg) were determined as described in Test Example 1.

As a results, it was shown that the survival rates of dimethyl-$\beta$-cyclodextrin (10 mg/kg) group, hydroxypropyl-$\alpha$-cyclodextrin (1 mg/kg) group, and hydroxypropyl-$\beta$-cyclodextrin (10 mg/kg) group were 27%, 27% and 33%, respectively, as compared with that of Ringer group which was 7%.

Test Example 5

The survival rates in the treatment with $\beta$-cyclodextrin polymer [product obtained by polymerizing $\beta$-cyclodextrin by crosslinker](1 mg/kg) and trimethyl$\beta$-cyclodextrin (1 mg/kg) were determined as described in Test Example 1.

As a results, it was shown that the survival rates of $\beta$-cyclodextrin polymer (1 mg/kg) group and trimethyl-$\beta$-cyclodextrin (1 mg/kg) group were 33% and 33%, respective as compared with that of Ringer group which was 13%.

The above results indicate that the compounds used in the invention have an excellent action in prolonging the life of a shocked subject.

What is claimed is:

1. A method for treatment of shock which comprises administering, to a subject in need of such treatment, a cyclodextrin or a derivative thereof in an amount effective in such treatment.

2. A method according to claim 1, in which the derivative is selected from the group consisting of an etherified cyclodextrin, a branched cyclodextrin, an acylated cyclodextrin and a sulfur-containing cyclodextrin.

3. A method according to claim 1, in which the derivative is dimathylcyclodextrin.

4. A method according to claim 1, for treatment of endoxin shock.

* * * * *

UNITED STATES PATENT AND TRADEMARK OFFICE
CERTIFICATE OF CORRECTION

PATENT NO. : 5,071,838
DATED : December 10, 1991
INVENTOR(S) : Ryuji Ueno

It is certified that error appears in the above-identified patent and that said Letters Patent is hereby corrected as shown below:

Claim 4, at column 6, line 28, delete "endoxin" and insert --endotoxin--.

Signed and Sealed this

Eleventh Day of May, 1993

Attest:

MICHAEL K. KIRK

Attesting Officer

Acting Commissioner of Patents and Trademarks